United States Patent [19]

Luccio et al.

[11] Patent Number: 4,598,415
[45] Date of Patent: Jul. 1, 1986

[54] METHOD AND APPARATUS FOR PRODUCING X-RAYS

[75] Inventors: Alfredo U. Luccio; Bertrand A. Brill, both of Shoreham, N.Y.

[73] Assignee: Imaging Sciences Associates Limited Partnership, Great Neck, N.Y.

[21] Appl. No.: 522,567

[22] Filed: Aug. 15, 1983

Related U.S. Application Data

[63] Continuation-in-part of Ser. No. 415,015, Sep. 7, 1982, abandoned.

[51] Int. Cl.⁴ .................. G21G 4/00; G21K 1/00; H01J 35/00; H05G 1/00
[52] U.S. Cl. .................. 378/119; 378/145; 378/210
[58] Field of Search .................. 378/119, 145, 210

[56] References Cited

U.S. PATENT DOCUMENTS

| | | | |
|---|---|---|---|
| 3,679,897 | 7/1972 | Hansen et al. | 250/251 |
| 3,746,860 | 7/1973 | Shatas et al. | 378/119 |
| 3,822,410 | 7/1974 | Madey | 378/119 |
| 3,886,366 | 5/1975 | Kash | 378/119 |
| 3,944,822 | 3/1976 | Dzubay | 378/145 |
| 3,955,089 | 5/1976 | McIntyre | 378/119 |
| 3,961,197 | 6/1976 | Dawson | 378/119 |
| 4,058,486 | 11/1977 | Mallozzi et al. | 378/119 |
| 4,109,218 | 8/1978 | Schneider et al. | 332/7.51 |

OTHER PUBLICATIONS

"Momentum Modulation of a Free Electron Beam with a Laser", Journal of Applied Physics, vol. 46, No. 1, Jan. 1975–pp. 132–137.
Instruments and Experimental Techniques, No. 4, Jul.–Aug. 1967, pp. 710–714.
Physical Review, vol. 138, No. 6B, 21 Jun. 1965, pp. B1546–B1549.
Il Nuovo Cimento, vol. 59B, No. 2, 11 Oct. 1980, pp. 247–256.

Primary Examiner—Alfred E. Smith
Assistant Examiner—T. N. Grigsby
Attorney, Agent, or Firm—Ostrolenk, Faber, Gerb & Soffen

[57] ABSTRACT

A method and apparatus for producing X-rays utilizing the Compton backward scattering effect. The X-rays are electronically steerable for scanning, and also have a very narrow angle of divergence for precise positioning. The X-rays have a narrow bandwidth, and are tunable to permit an object to be irradiated with only the desired beneficial radiation. The X-rays are polarized for trace element analysis. The X-rays are suitable for medical diagnostic and therapeutic, and industrial testing, purposes.

43 Claims, 7 Drawing Figures

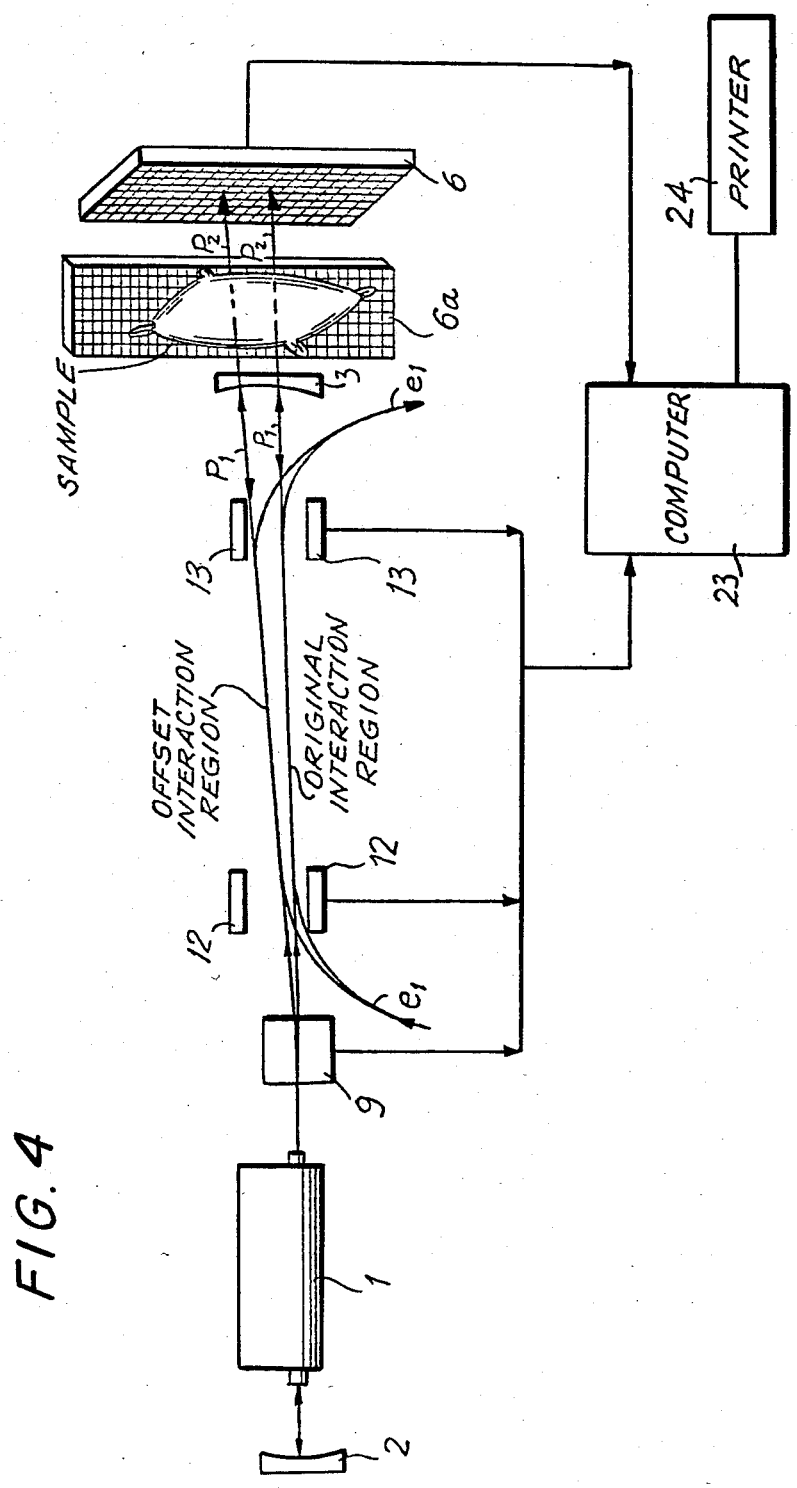

METHOD AND APPARATUS FOR PRODUCING X-RAYS

CROSS-REFERENCE TO RELATED APPLICATION

The present application is a continuation-in-part of application Ser. No. 415,015, filed Sept. 7, 1982, now abandoned.

BACKGROUND OF THE INVENTION

1. Field of the Invention

The present invention generally relates to the production of X-rays and, more particularly, to a method of and arrangement for producing X-rays by the Compton scattering effect in a desired frequency range suitable for medical diagnostic and therapeutic, or industrial testing, purposes. Still more particularly, this invention relates to a novel method of and apparatus for electronically steering an X-ray beam, as well as to a method of and apparatus for X-raying an object with a narrow band frequency characteristic.

2. Description of the Prior Art

Conventionally, X-rays are generated for medical diagnostic purposes by using a cathode tube, wherein a stream of electrons is directed towards a metal plate for impingement thereon, to thereby cause the metal material to emit radiation in the X-ray range which, for diagnostic purposes, lies in the range from about 20 Kev. to 100 Kev. Since this process depends on the excitation of the shell electrons of the metal and on spontaneous level change within the atom shell envelope, accompanied by sudden energy release in the form of X-rays, the characteristics of individual X-ray photons cannot be determined. The conventional X-ray tube emits a highly divergent X-ray beam with a distribution of the frequencies or energy levels of the photons in the X-ray beam over a very wide range. To protect the operating personnel and/or the patient from undue exposure to X-rays, it is necessary to shield or mask the X-ray apparatus, so that the issuing beam will only cover the desired area to be X-rayed. Mechanical shutters are used to control the emission angle.

The use of a conventional X-ray tube for medical diagnostic purposes is far from an ideal situation, since the shielding is rarely perfect and, moreover, only a fraction of the produced X-rays is available for the desired use. The situation is further aggravated by the fact that the X-ray beam is distributed over a very wide X-ray spectral range, so that the object being X-rayed, be it an article to be tested, examined or analyzed, or a portion of a body of a patient to be examined or subjected to radiation therapy, is exposed not only to the X-ray radiation of the most beneficial energy level, but also to X-rays having energy levels outside the beneficial range. Thus, the exposure of the object to X-rays or, in other words, the dosage of the X-ray radiation, is far in excess of the necessary level since, in order to achieve the desired dosage of the beneficial X-ray energy level, the object is simultaneously exposed to a substantial dosage of X-ray radiation outside the beneficial range.

For radiation therapy purposes, X-rays in the range from about 10 Kev to about 250 Kev are used and, conventionally, for the higher energy range, a linear accelerator may be used to accelerate a stream of electrons against a metal plate to cause X-ray emission. However, the very same drawbacks described above are still present, because the issuing high energy X-rays also have a wide angle beam and a broad band frequency characteristic.

For elemental analysis purposes, polarized X-rays are desired. Conventionally, polarized X-rays are produced by passing unpolarized X-rays through materials, such as graphite. However, this is a very inefficient process. In medical radiography, polarized X-rays have never, to our knowledge, been used and, hence, their potential utility remains to be explored.

In the field of physics research, large electron storage rings which accelerate electrons around a closed loop are utilized to generate polarized X-rays as a byproduct of the electron acceleration and deceleration process. However, these large electron storage rings are massive installations, are present at only a few locations around the world, and are not practical for use in medical or industrial applications.

Still another drawback of conventional X-ray apparatus is that the X-ray beam itself has never been electronically steered. It is well known that X-ray scanning of a patient is a highly desirable medical technique and, hence, the conventional techniques to accomplish scanning are to mechanically move the patient, or to mechanically move the X-ray tube itself, or to mechanically move the exit shutter of the X-ray apparatus. In some hospitals, there are huge X-ray machines which place the patient on a table, and move the patient in a desired direction. Also, the patient can remain stationary, and the X-ray machine can move around the patient. All of these prior art techniques are very cumbersome and unwieldy and, most importantly, are slow, i.e. on the order of 15-20 seconds or more and, hence, patient movement can cause X-ray blur.

It is also known in the field of nuclear physics research to use the Compton backward scattering effect for producing gamma rays, i.e. high energy photons which lie in the multi-Mev to Gev region. Briefly summarized, the Compton effect is characterized as follows: An incoming photon supplied by a light source, such as a laser, is collided with an incoming electron supplied by an electron accelerator. The result of the collision is that the electron loses energy, and the photon gains energy. The outgoing or deflected photons have a very high energy level, and typically are in the gamma-ray range identified above. The Compton effect, to the best of our knowledge, has never been used to generate X-rays for bio-medical and industrial investigations.

SUMMARY OF THE INVENTION

Objects of the Invention

Accordingly, it is the general object of this invention to avoid the above-described drawbacks of the prior art.

Another object of this invention is to produce X-rays in a desired range suitable for medical diagnostic, or medical therapeutic, or industrial testing purposes.

An additional object of this invention is to reliably and controllably produce X-rays in a novel manner.

Another object of this invention is to generate X-rays whose individual photon characteristics can be determined with high accuracy. A further object of this invention is to protect medical or industrial operating personnel of X-ray apparatus from undue exposure to X-rays without requiring massive and extensive shielding.

Still another object of this invention is to expose a patient to be X-rayed to the most beneficial range of X-ray radiation without unduly exposing the patient to radiation outside the beneficial range.

Still a further object of this invention is to reliably and controllably select the X-ray frequency band to irradiate an article or person to be X-rayed.

Yet another object of this invention is to efficiently generate polarized X-rays for elemental analysis, as well as for medical applications.

Yet an additional object of this invention is to provide essentially electronic means for steering an X-ray beam to achieve scanning, rather than by mechanically moving the X-ray apparatus and/or the patient.

Another object of this invention is to utilize the Compton backscattering effect for bio-medical and industrial applications.

Another object of this invention is to incorporate a single apparatus for use as a low radiation dosage diagnostic device and for purposes of planning a course of treatment, as well as a high radiation dosage therapy device. This can be achieved either by use of tuned X-ray frequencies in photon activation therapy, or by use of the electron beam itself.

A further object of this invention is to precisely locate where in a sample a scattering process occurred.

SUMMARY OF THE INVENTION

In keeping with these objects and others which will become apparent hereinafter, one feature of the invention resides, briefly stated, in a method of, and apparatus for, producing X-rays in a desired range suitable for medical diagnostic and therapeutic, or industrial testing, purposes. As described below, this desired range lies from about 0.5 Kev to about 250 Kev. In accordance with this invention, a multitude of incoming electrons at a predetermined energy level is passed in one direction along a predetermined path through an interaction region; and a multitude of incoming photons at a predetermined energy level is directed along a direction substantially opposite to the one direction through the interaction region and into colliding relationship with the incoming electrons. In accordance with the Compton effect, the resulting interaction between the incoming electrons and the incoming photons causes, inter alia, outgoing photons at an increased energy level to be propagated substantially along the one direction towards an object to be X-rayed. The object can be animate or inanimate. The increased energy level of the photons lies within the above-described desired range characteristic of X-rays. The energy level of the incoming electrons is carefully controlled to propagate the outgoing photons as X-rays.

In its broadest sense, the novelty of this invention resides in the recognition, for the first time, that photons of much lower energy than those ordinarily produced in nuclear physics research can be generated using the Compton backscattering effect by carefully controlling the energy level of the incoming electrons. By generating photons in the X-ray range, the resulting X-rays can be used for many applications including, but not limited to, medical diagnosis, radiation therapy, elemental analysis, industrial radiography.

Another feature resides in the fact that the X-rays produced by this invention are emitted as a very narrow angle beam. The highly directional nature of the X-rays tends to reduce, although not entirely eliminate, the need for mechanical shutters, shielding, etc. It also is highly desirable when combined with the scanning feature described in detail below.

Yet another feature is embodied in the fact that the X-rays produced by this invention are emitted in a very narrow frequency band. Inasmuch as the emitted X-rays of conventional apparatus unavoidably have a broad band frequency characteristic, the object is typically exposed to an unduly large dose of X-rays. It will be appreciated that only a narrow range of the X-ray spectrum is typically required for any particular irradiation. Hence, a patient need only be irradiated with that particular beneficial range. The fact that the conventional X-rays also contain frequencies outside of the beneficial range is very undesirable, and represents a potential source of overdosage and side effect problems. The narrow band frequency characteristic of the X-rays produced by this invention overcomes all of these disadvantages.

Indeed, another related feature lies in the tunability aspect, whereby the particular narrow band frequency in the X-ray spectrum can be selected by the operator. A physician, for example, can select the X-ray frequency most beneficial for a particular procedure. In the prior art, no such tuning control exists.

As noted above, the scanning of X-ray beams in the above-identified desired range has been implemented by slow mechanical arrangements, but not by electronically deflecting the X-ray beam. This invention has realized a significant breakthrough in the X-ray scanning field. It will be appreciated that X-ray beams in the desired range, unlike electrons, consist of uncharged particles which cannot be electronically, magnetically or optically deflected. This invention proposes to electronically steer the X-ray beam by varying the position in space of the interaction region. In a preferred embodiment, the incoming photons of very low energy are optically deflected by an electronically controlled optical scanner, and the incoming electrons are magnetically deflected by a magnetic arrangement. The deflections of the photons and electrons must be carefully controlled so that they are always directed along coincident paths. Hence, the X-ray beam has been displaced not by deflecting the X-ray beam itself, but by moving the interaction region.

Still another feature resides in the fact that the Compton-generated X-rays are polarized. In medical radiography, polarized X-rays have never been used and, hence, their potential utility remains to be explored. However, in medical in vivo trace element analysis applications and industrial applications for which polarized X-rays are desired, this invention increases the sensitivity of the method and avoids the conventional inefficient graphite-mediated process described above.

The novel features which are considered as characteristic of the invention are set forth in particular in the appended claims. The improved X-ray apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 4 is a diagrammatic top plan view showing the main components of the apparatus of FIG. 2 and their cooperation during scanning operation.

DETAILED DESCRIPTION OF THE PREFERRED EMBODIMENTS

Figure 1:
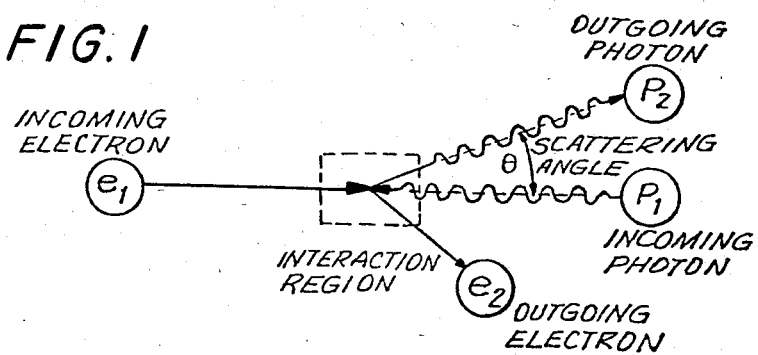
FIG. 1 is a diagrammatic view illustrating the principle of the Compton backscattering effect.

Referring now to the drawing in detail, the Compton backward scattering effect which has been used in the field of nuclear physics research for producing high energy photons in the gamma ray range has been schematically represented in FIG. 1. A multitude of incoming electrons schematically represented by the incoming electron $e_1$ is directed in one direction to an interaction region. A multitude of incoming photons schematically represented by the incoming photon $p_1$ is directed in the opposite direction to the interaction region. If the incoming photon having a quantum energy level $\epsilon_1$ collides with the incoming electron having a kinetic energy level E, then the incoming photon gains energy and increases to a quantum energy level $\epsilon_2$ at the expense of the incoming electron which loses energy during the collision interaction. The result of the interaction is that the incoming electron which lost some, but very little, of its energy is deflected along the illustrated trajectory of the outgoing electron $e_2$, and the incoming photon $p_2$ which gained in energy is deflected along the illustrated trajectory of the outgoing photon $p_2$. The outgoing photons are propagated substantially backwardly in the opposite direction to that of the incoming photons. As shown in FIG. 1, the outgoing photons are deflected within a scattering angle $\theta$ to form a cone-shaped beam. The scattering angle is grossly exaggerated in FIG. 1; in reality, this angle is very close to zero degrees such that the outgoing photon trajectory is almost co-linear with the incoming photon trajectory. In addition, the illustrated trajectory for electron $e_2$ is also grossly exaggerated. In fact, at the energy levels to be hereinafter discussed, electron $e_1$ will lose so little during collision with photon $P_1$ that deflection thereof resulting from collision with photon $P_1$ will not deflect electron $e_1$ from the narrow electron beam in which electron $e_1$ traveled prior to colliding with photon $P_1$.

The above-described Compton effect has so far been used only in nuclear physics to conduct fundamental research using gamma rays. The instant invention is based, in its broadest sense, on the recognition that X-rays can be generated by the Compton effect, and that these X-rays could be used in many applications, and particularly in the medical diagnostic and therapeutic fields of medicine. As used throughout the specification and claims herein, X-rays may be defined as photons falling in the range from about 0.5 Kev to about 250 Kev. More particularly, the range from about 20 Kev to about 100 Kev, and particularly the lower end of the range, is best for medical diagnosis, with 40 Kev being typical for such standard applications as chest X-ray examinations. In radiation therapy, the low energy range of 10 Kev to about 30 Kev is best suited for X-ray radiation therapy of superficial tumors or for photon activation therapy, whereas the higher energy range from 30 Kev to 250 Kev is used for treatment of deeper tumors. In elemental analysis by X-ray illumination, the range from about 0.5 Kev to about 100 Kev is best. It will be expressly understood that the numerical values and ranges for particular fields of use identified above are merely exemplary, and have been provided as the currently preferred values. Some degree of overlap may exist, and new developments in medicine may expand these ranges.

Figure 2:
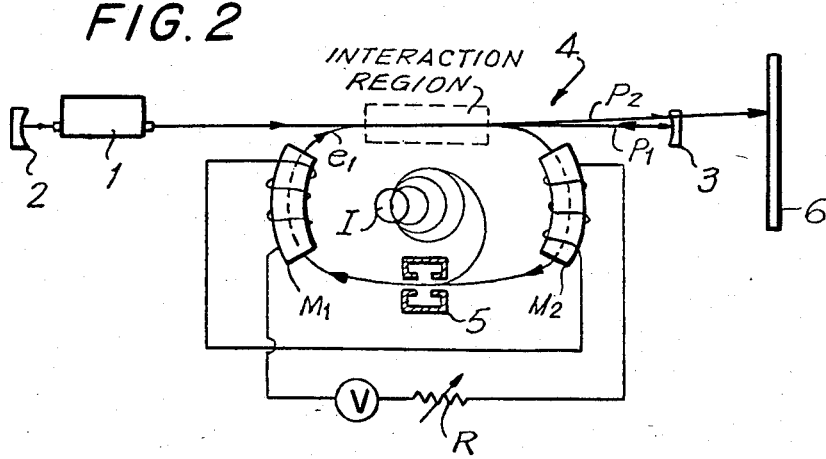
FIG. 2 is a somewhat simplified schematic diagram of an X-ray apparatus according to the present invention.

Turning now to FIG. 2, an apparatus for producing X-rays in the above-identified desired range suitable for medical diagnostic and therapeutic, or industrial testing, purposes in accordance with the method of this invention comprises a laser source 1 operative for emitting photons, either in a continuous or pulsed manner, in an optical cavity bounded by a rear reflecting concave mirror 2 and a front reflecting concave mirror 3. The mirrors 2,3 reflect low energy photons, that is photons having an energy level below that of X-rays. As described below, the mirrors are transmissive to X-rays. The low energy photons are reflected back and forth between the mirrors 2,3. The photons reflected off the front mirror 3 and directed from right to left across the designated interaction region correspond to the incoming photons shown in FIG. 1.

As for the electrons, any electron accelerator, but particularly one that can supply high current, good stability, and good beam quality such as a compact storage ring 4, can be used to accelerate the electrons around a so-called racetrack that is composed of straight and circular sections. A pair of arcuate bend electromagnets M1 and M2 are situated at the spaced-apart circular sections of the racetrack, and are operative to magnetically act on the electrons to cause them to repeatedly circulate at a predetermined energy level E along the closed loop. The electromagnets have windings which are electrically connected in series and to a voltage supply V and a variable control resistor R. For start-up purposes, electrons can be introduced into the storage ring by many different types of injectors. The injector illustrated is a microtron I which is operative to move the electrons at initial low kinetic energy levels along a trajectory consisting of circles having increasing diameters and being tangent to each other at a common point. This electron trajectory spirals outwardly to eventually intersect with a straight section of the racetrack, whereupon the now higher kinetic energy electrons are caused to circulate around the racetrack in a narrow beam for very long time periods on the order of hours. A high beam current is obtained by repeated injection and stacking of a plurality of pulses of electrons. Once the desired beam current is obtained, the injector can be shut off or, if desired, the injector can be used independently to irradiate an object with a stream of electrons. A radio frequency cavity 5 is also positioned in a straight section of the racetrack to restore lost energy to the circulating electrons during each revolution, because there are unavoidable attenuation losses. Position detectors (not shown) may be used to monitor the position of the electrons along the racetrack.

The electrons directed from left to right in FIG. 2 across the interaction region correspond to the incoming electrons of FIG. 1. The interaction region is situated in a straight section of the racetrack. The incoming electrons and photons are directed in opposite directions towards each other to cause the Compton collision.

After the Compton collision in the interaction region, the outgoing electrons lose energy, but at the energy levels under consideration the electrons lose so little energy during Compton collision that such electrons continue traveling around the storage ring in the same narrow electron beam that such electrons traveled in prior to collision. The outgoing photons gain energy, and are propagated towards the right within a cone-shaped beam having a small divergence angle, typically less than 0.01 radians. The cone-shaped beam axis is coincident to the incoming photons in the interaction region. The outgoing photons of increased energy, i.e. X-rays, pass right through the front mirror 3 and impinge on a target 6. Any object, animate or inanimate, may be placed in front of the target 6. The object may be any article to be tested, examined or analyzed, or a portion of a body of a patient to be examined or subjected to radiation therapy. The target 6 may be X-ray film, or position sensing devices sensitive to X-rays, just to mention a few possibilities.

The energy $\epsilon_2$ of the scattered or outgoing photon is related to the energy $\epsilon_1$ of the incoming photon by the following equation:

$$\epsilon_2 = 4\rho\gamma^2\epsilon_1$$

with $$\epsilon_2 = h\nu_2/mc^2$$

$$\epsilon_1 = h\nu_1/mc^2$$

$$\gamma = E/mc^2$$

$$\rho = (1 + \gamma^2\theta^2 + 4\epsilon_1\gamma)^{-1}$$

where
h = Planck's constant
$\nu_2$ = frequency of outgoing photons
$\nu_1$ = frequency of incoming photons
$mc^2$ = rest mass-energy of the electron (0.511 Mev)

We have recognized from the foregoing equation that the energy of the outgoing photons can be varied as a function of the electron energy. Hence, by controlling the electron energy, for example by adjusting the continuously variable resistor R, the kinetic energy of the electrons can be changed, and concomitantly, the energy of the outgoing photons can be adjusted to the desired X-ray range. By changing the resistance of the resistor R, the current to the electromagnetic windings is varied and, in turn, the magnetic field acting on the electrons is changed and, in turn, the radio frequency cavity cooperates with the changed magnetic field to change the kinetic energy of the electrons.

By way of example, if the production of 40 Kev photons, i.e. the X-rays used for chest examinations, is desired, then the electron energies and parameter values listed in Table I have been calculated for various types of laser sources.

TABLE I

| ELECTRON ENERGIES FOR PRODUCTION OF 40 Kev X-RAYS FOR VARIOUS LASERS | | | |
|---|---|---|---|
| LASER TYPE | ARGON | Nd Yag | $CO_2$ |
| WAVELENGTH ($\mu$m) | 0.5 | 1 | 10 |
| $h\nu_1$(eV) | 2.48 | 1.24 | .124 |
| $\gamma$ | 64 | 90 | 284 |
| E(MeV) | 32 | 45 | 142 |

In nuclear physics research, the typical laser used is an argon laser which emits visible light at about 3 watts of continuous power. This power level is too low for medical diagnostic or radiation therapy techniques. Of course, for nuclear physics research, higher powers are not required. Furthermore, in nuclear physics research, huge, massive, large-sized storage rings operate with incoming electron energies in the range from about 300 Mev to about 8 Gev. The conventional storage ring can have a perimeter on the order of 50 meters, and can have from 8 to 48 electromagnets arranged around the racetrack. The gamma rays produced can be anywhere in the multi-Mev to Gev region.

By contrast, the laser used in the present invention is preferably a $CO_2$ laser or a Nd Yag laser which emit infrared light at much higher levels of power. A $CO_2$ laser can emit infrared light at about 10 kilowatts of average power; the Nd Yag laser can emit infrared light at about 1 kilowatt of average power. Moreover, as shown in FIG. 2, only two bend electromagnets M1 and M2 are used. Rather than a 50 meter perimeter for the racetrack, this invention uses a compact storage ring of about 10 meters in perimeter. Rather than accelerating the electrons to energy levels on the order of billions of electron volts, the electrons are accelerated to much lower levels. For example as shown in Table I, to produce X-rays at the 40 Kev level, the electron energy levels required are in the 32 Mev to 142 Mev range for the various lasers listed.

As noted previously, the laser can be operated in a continuous or pulsed mode. The pulsed mode is preferred, because it increases the effective power of the laser. In the storage ring, the electrons are confined in one or more bunches. Hence, it is desirable to synchronize the laser pulse with the electron current pulse so that collisions start at the beginning of the interaction region for each revolution of the electrons. Inasmuch as the Compton collisions are relatively few, the effective power can be improved greatly when the same laser pulse is used over and over by making it repeatedly oscillate between the pair of mirrors 2,3 of the optical cavity. This decreases the repetition rate out of the laser itself. Preferably, the laser is designed to produce pulses which are twice the length of the interaction region. To provide proper synchronization between the laser pulse and the electron bunch, the length of the optical cavity is equal to one-half the perimeter of the storage ring, in the case where the storage ring operates with only a single electron bunch. A laser pulse interacts several times with the electron bunch, and is only attenuated in the reflections on the mirrors. Depending on the wavelength of the laser, the attenuation per pass can be made very small, on the order of a fraction of 1%, so that a large number of passes through the interaction region may be obtained before a new laser pulse is required. The attenuation of the electron bunches due to Compton collisions is also very small, such that the electron beam lifetime is very long, and may be on the order of hours.

Figure 3:
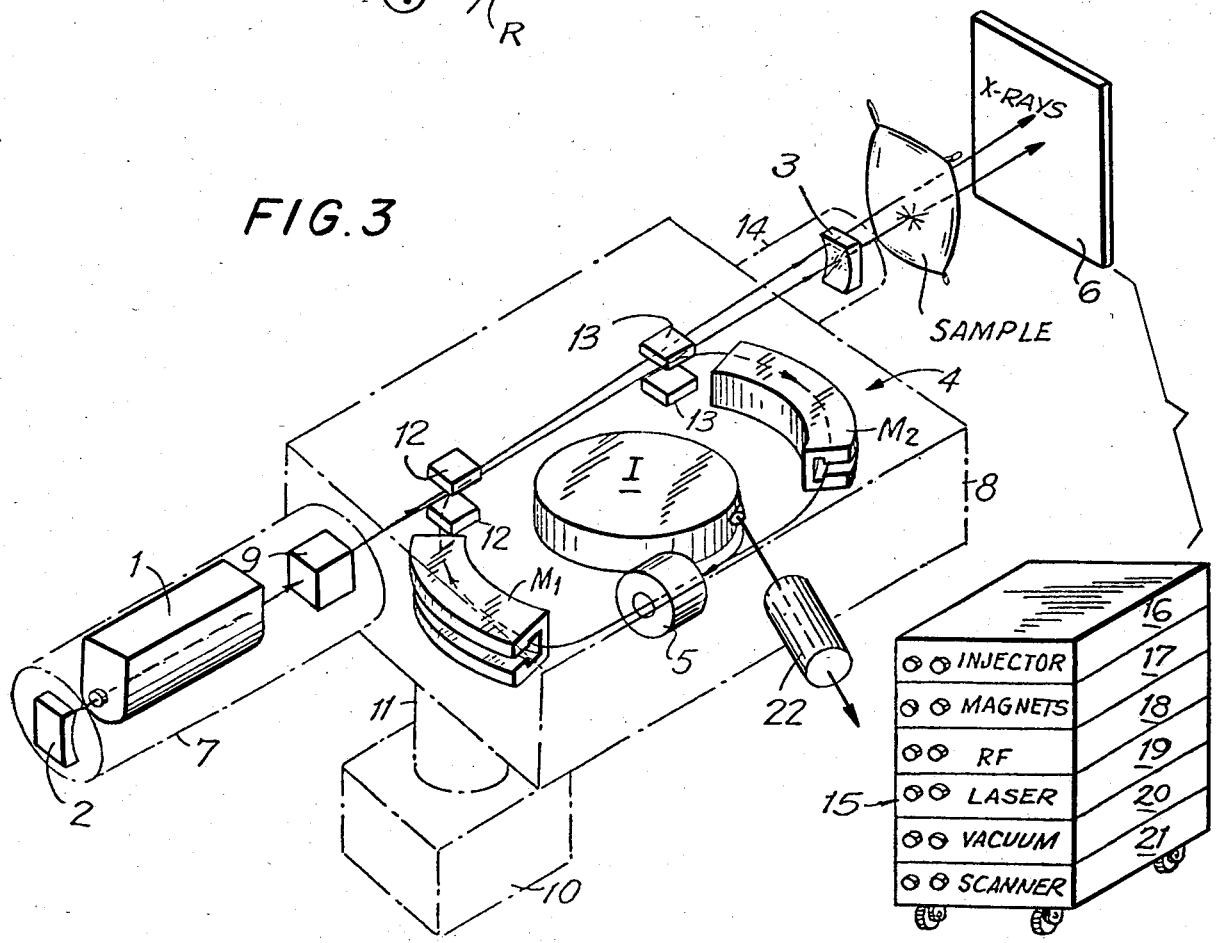
FIG. 3 is a perspective view of a preferred embodiment of the apparatus shown in FIG. 2.

Turning now to FIG. 3, a simplified perspective view of the compact X-ray apparatus of FIG. 2 is shown, with various components removed for the sake of clarifying the drawing, and with various other components added to show still other features of the invention. Specifically, as shown in FIG. 3, the laser source 1 is situated in a tubular extension 7 which is supported at one side of a vacuum enclosure or main housing 8. The rear mirror 2 is situated at the far end of tube 7, and an optical scanner 9, as described below, is situated at the other end of the tube. A vacuum ion pump system 10 including a connecting conduit 11 communicates with the interior of the main housing 8, and is operative to evacuate the interior thereof to a high vacuum condition, typically on the order of more than $10^{-9}$ torr for long electron beam life.

The storage ring 4, radio frequency cavity 5, the injector I and the pair of curved bend electromagnets M1 and M2 are all operative as described previously in connection with FIG. 2. A pair of deflecting magnet devices 12,13 are located at opposite ends of the interaction region, and their operation in cooperation with the optical scanner 9, is described below in connection with FIG. 4. The front reflecting mirror 3 may be mounted within the main housing, or in another extension tube 14 located at the other side of the main housing 8. A sample to be X-rayed may be located directly in front of the target 6. The sample may represent a patient, and the target may be analog X-Ray film or digital X-ray sensitive detectors.

As noted previously, the injector need not be operative after the current has reached its desired level. The injector need not be shut down thereafter, because it can still serve as an independent source of electrons for irradiation applications. A non-illustrated extracting magnet assembly at the outlet port of the injector can be energized to deflect the electrons out of their usual insertion path into the closed loop outwardly through the discharge port 22.

A control unit 15 having a plurality of control modules is electrically connected by wiring (not illustrated for the sake of clarity) to the various components of the X-ray apparatus. For example, module 16 supplies power to the injector; module 17 supplies power to the bend magnets M1 and M2; module 18 supplies power to the radio frequency cavity 5; module 19 supplies power to the laser; module 20 supplies power to the ion pump 10; and module 21 supplies power to the optical scanner 9 and the deflecting magnets 12, 13. The control unit 15 is mounted on a wheel-mounted frame for ease of movement.

The X-ray apparatus shown in FIG. 3, except for the control unit, is a relatively compact arrangement, and occupies a space about 100 to 200 cubic feet in volume. The small size of the arrangement allows it to be conveniently used in a hospital or industrial setting.

Turning now to FIG. 4, this is an enlarged view of the interaction region and those components of the apparatus which vary the direction of propagation of the X-rays to scan the object. Inasmuch as an X-ray beam consists of uncharged particles which cannot be electronically or magnetically deflected, it is believed that this invention represents the first time that an X-ray beam has ever been electronically steered. Of course, as noted above, X-ray beams have been used in various mechanical scanning arrangements, but they are all too slow, are cumbersome, are unwieldly, and are susceptible to blur due to patient movement. The components of FIG. 4 provide a very fast electronic scanning which avoids all these drawbacks.

Essentially, the X-ray scanning is performed by changing the spatial position of the interaction region. As the interaction region is moved, so the direction of propagation of the X-rays is changed. The X-ray beam itself is not deflected, but the photon beam and the electron beam are deflected. Specifically, deflecting magnets 12,13 are positioned adjacent the electron path at the opposite ends of the interaction region, and are operative, when energized by control module 21, to deflect the electrons out of their normal path in the original interaction region to an offset path. Preferably, the deflector 13 deflects the electrons to a greater extent than the deflector 12 so as to define an inclined offset path, rather than the more horizontal original path. It will be recalled that electrons are charged particles which can be magnetically deflected.

At the same time, the photons are optically deflected by the optical scanner 9 such that the incoming photons will collide with the electrons in their new offset inclined path. The X-rays are generated at the new offset interaction region. The optical scanner 9 and the deflectors 12,13 must be carefully controlled electronically such that the photon path is coincident with the electron path for each offset path position. As illustrated, the original and offset interaction regions represent the end-limiting positions of a scan. It will be appreciated that there are a plurality of intermediate interaction regions between the illustrated end-limiting positions.

The electronic steering permits the operator to precisely steer the X-ray beam at exactly the area of interest and at high scanning rates. X-ray blur would be reduced not only by the fast scanning speeds, but also by new digital detector techniques, as described below. The narrow angle beam width cooperates with the scanning feature to give very accurate and precise positioning control for improved diagnosis and radiation therapy where fine control is critical for patient safety.

As previously described, the Compton-generated X-rays are emitted as a very narrow angle conical beam whose scattering angle $\theta$ typically does not exceed 0.01 radians. The number n of outgoing photons produced per unit time in a conical solid angle beam is proportional to the number $N_L$ of incoming photons that interact with the electrons, to the number $N_E$ of the electrons, to the frequency f of encounters, and to the cross-section $\sigma$ of the scattering process, and is inversely proportional to the common geometrical cross-section $\eta$ of the electron and photon beams.

Four of these quantities define the luminosity (L) characteristic by the following equation:

$$L = (N_e N_L / \eta) f$$

The number of photons produced per unit time is defined as:

$$n = L\sigma$$

Hence, it will be seen that the Compton cross-section is a function of the scattering angle $\theta$, and that the higher the electron energy, the more the scattered photons are contained in a narrow cone around $\theta = 0°$.

By way of example, for a $CO_2$ laser, whose electron energy is 142 Mev (See Table I), approximately 93% of the outgoing X-ray photons is contained in a conical beam of about 0.01 radians half-angle.

The highly directional nature of the X-rays generated herein tends to reduce, but not entirely eliminate, the need for shielding. Also, it is of great importance in steering the beam during the scanning mode, because the position of a highly directional beam is known with certainty, as opposed to the broad beam patterns of conventional X-ray equipment.

In accordance with a preferred embodiment, the target 6 is a detector array composed of a matrix of X-ray sensitive detectors operative for generating an electrical counting signal proportional to the flux, or number of photons per unit time, impinging on each detector. At the same time, the optical scanner 9 and magnetic deflectors 12,13 used to steer the X-ray beam generate an electrical steering signal indicative of the position of the X-ray beam.

The counting signal, and the steering signal are then conducted to a data acquisition computer 23 which processes these signals and converts them to data indicative of where a scattering interaction may have occurred in the sample under investigation. The data can be displayed on any convenient display such as printer 24. Quite apart from the Compton interaction described previously to generate the X-rays, another Compton interaction may occur in the sample, whereby the X-ray photons may collide with electrons in the sample and undergo a Compton reaction. The location of the scattering interaction in the sample could not be determined with precision heretofore, because the energy of the individual photons in the scanning beam could not be ascertained. The present invention can determine the energy of the individual photons and, hence, greatly advances the field of three-dimensional radiography.

The detector array may constitute a substantially planar main detector or plate 6 located rearwardly of the object to thereby perform two-dimensional radiography or, in another embodiment, a plurality of substantially planar auxiliary detectors, e.g. detector 6a, can be located at various locations around the object to thereby perform three-dimensional radiography. A pair of auxiliary detectors 6a can be arranged at opposite sides of a patient, and the main detector 6 can be arranged behind the patient. In another embodiment, a curved detector which extends circumferentially around the patient, either completely or partially about the patient, can be used instead of a plurality of planar detectors.

Figure 5A:
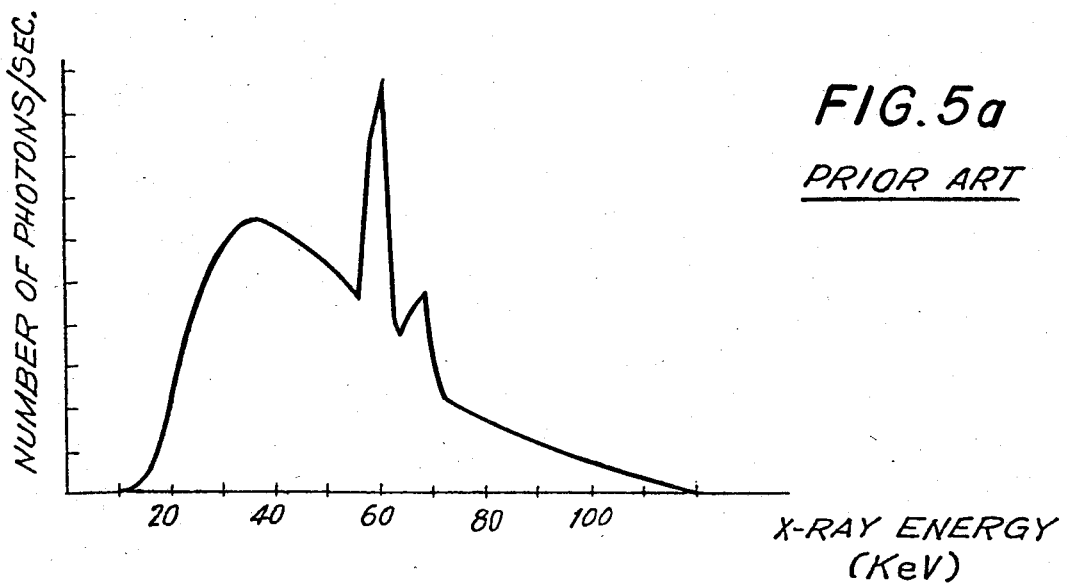
FIGS. 5a, 5b and 5c are graphic representations of the characteristic emission curves of a conventional X-ray tube, a synchrotron, and the apparatus according to the present invention.

Turning now to FIG. 5a, the emitted X-rays of a conventional X-ray tube have a broad band frequency characteristic. As shown, the conventional tube output is a continuum of freqeuncies plus so-called characteristic lines at particular frequencies or energy levels.

Figure 5B:
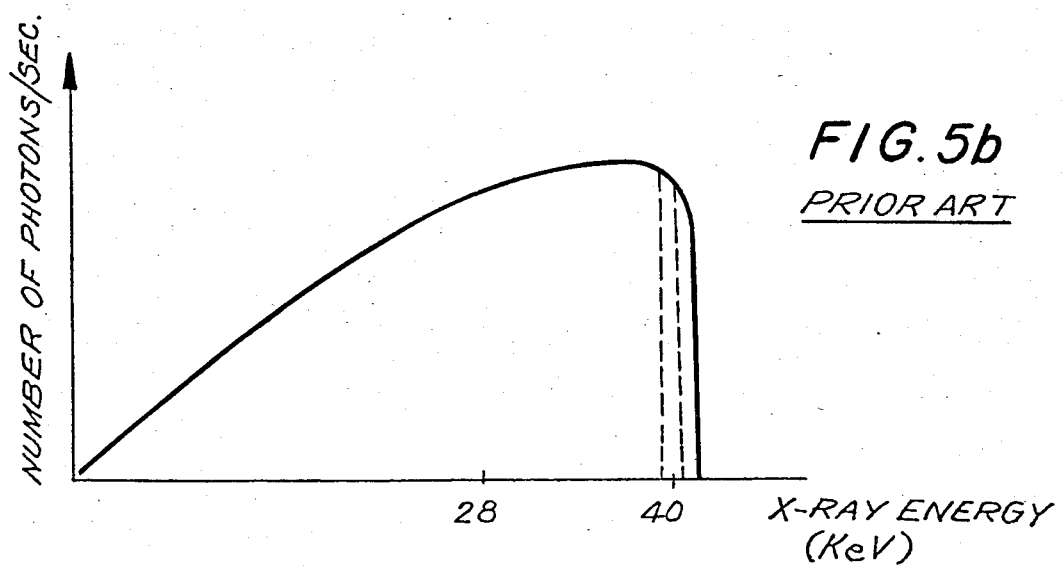

A similar broad band frequency characteristic without the characteristic lines is shown in FIG. 5b which illustrates the output of a conventional synchrotron. In the event that a physician wishes to irradiate a patient witn 40 Kev for a chest X-ray examination using the conventional X-ray tube or synchrotron, the patient will not only be exposed to the beneficial range of frequencies in the vicinity of 40 Kev, but will also be exposed to frequencies outside of the beneficial range. The patient is therefore exposed to non-beneficial or unwanted radiation. This can lead to undesirable side effects and overdosage.

Figure 5C:
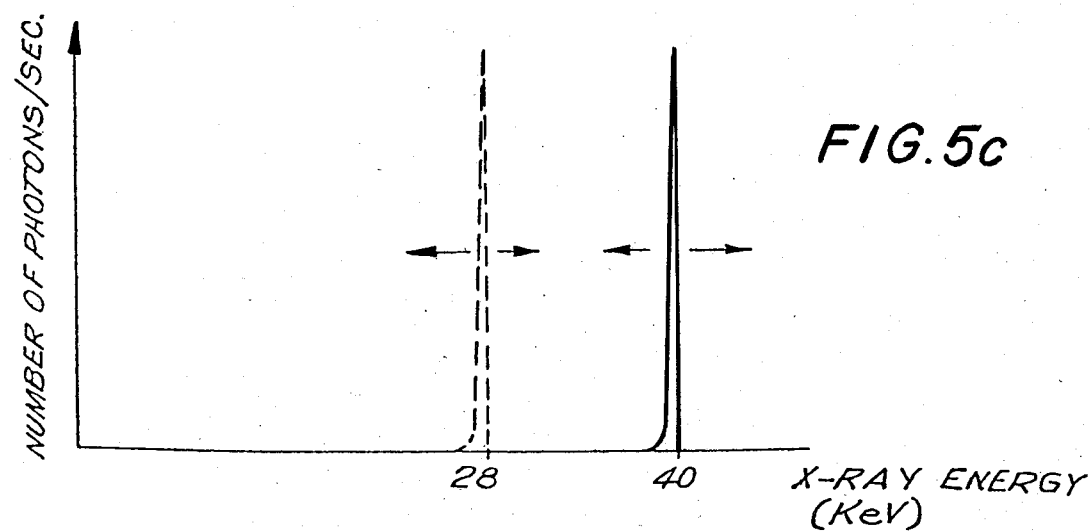

By contrast, the X-rays generated in accordance with this invention have a narrow band frequency characteristic. As shown in FIG. 5c, the frequency band around 40 Kev is very narrow, typically on the order of ±0.5%. The X-ray output is not a broad continuum. The patient is not exposed to unwanted, non-beneficial radiation, but only to the desired radiation.

Still another important aspect of this invention is the tunability of the X-rays, that is, the ability to produce X-rays of selected energies. For example, a radiograph of the chest synthesized from images using 40–50 Kev and 90–100 Kev X-rays can be produced which reveals either the bony structures in the chest, or the soft tissues, or both superimposed in the same image. By the choice of two or more energies, images can be synthesized to reveal bone, soft tissues, or fat due to their different attenuation properties at different X-ray energies. Images made at energies above and below the k-absorption of injected contrast agents also provide enhanced contrast at minimum radiation exposure of the patient. Multiple energy images can also be useful in industrial radiography where impurities or flaws need to be detected.

In accordance with this invention, this tunability is achieved by changing the energy of the incoming electrons in the storage ring by changing the magnetic flux of the electromagnets M1 and M2. This is performed, according to preferred embodiment, by varying the resistance of the variable resistor R (see FIG. 2) which, in turn, changes the current to the windings of the electromagnets and, hence, the magnetic flux. Another technique is to use split permanent magnets and to move the two halves of each magnet towards and away from each other by a mechanical drive device.

As also shown in FIG. 5c by the diagrammatically-illustrated arrows, the operator can tune the output of the X-ray apparatus to 28 Kev or, at his option, to 40 Kev, for that matter, to any energy level. The variable resistor is an analog control device for fine tuning. If desired, digital control devices can be used to select particular energy levels of frequent interest.

The tunability feature permits a single X-ray apparatus to generate X-rays for many purposes. Now, an operator can use the same apparatus for both diagnosis and for radiation therapy. This versatility is a very cost-effective solution to physicians, hospitals and industry having small capital budgets and limited working areas.

The X-rays produced by this invention are nearly completely polarized. The polarization P is calculated as follows, with $\gamma$ defined above and $\theta_c$ being the collimating half angle of the scattering angle:

$$P \approx 1 - (\gamma \theta_c)^4$$

Hence, by way of example, for $\gamma = 284$ (See Table I for the $CO_2$ laser) and a collimating angle $\theta_c$ of about 0.5 milliradians, the polarization is about 100%. In conventional X-ray tubes, polarized X-rays are not produced and, hence, they have never been used in medical radiography. However, there are medical, industrial, and trace element analysis applications for which polarized X-rays are desired, and for which the present invention is of particular utility.

For example, trace elements can be measured and their distribution imaged in vivo and in vitro from their characteristic X-ray spectra. In vivo measurements are greatly enhanced in sensitivity using polarized X-rays since it is then possible to reject scattered radiation arising in thick samples (parts of body). The measurement of iodine in the thyroid is best carried out using X-ray energies closely matched to the binding energy of the k-shell electrons ($\approx 32$ Kev). Detection and quantitation of various high atomic number elements in the body can be established using appropriately-chosen X-ray energies. Thus, elements such as lead, cadmium, mercury, and arsenic have been measured using different exciting sources. The use of tuned energy polarized X-rays permits optimized multi-element trace element analysis for biological as well as industrial materials.

As noted previously, the conventional technique of passing unpolarized X-rays through graphite, for example, to produce polarized rays is a very inefficient process. This invention obviates these drawbacks.

In summary, the X-rays produced by this invention are not only generated in a novel manner, but are highly directional, tunable, narrow band, monochromatic, scannable, and polarized. All standard X-ray applications can be achieved with the X-rays produced by this invention. Chest X-rays, mammography, pediatric X-rays, etc. can all make particular use of the scannability of the X-rays. Cardiac and vascular studies are benefited by the fixed or non-scanning mode of operation. In cancer research, the incorporation of elements such as iodine into nucleic acid by the administration of an iodinated nucleotide precursor of thymidine permits certain cancer cell tumors to be preferentially irradiated. Tunability of the X-rays is of special importance in this respect (photon activation therapy) and, particularly, if different tumors require different elements and, hence, X-rays of different energies.

Computer tomography systems used in medicine or industrial non-destructive testing image the 3-dimensional distribution of electron density by differential transmission of one or more X-ray energies. These systems require the transmission of X-rays from multiple angles through the body and the rotation of heavy machines around the subject which takes relatively long times ($\geqq 2$ seconds). The measurement of Compton-scattered radiations from the body is made during exposure to scanning beams made up of tunable X-rays. Since the energy of each X-ray is known with precision (from the concurrent measurement of electron energy associated with its generation), it is possible to reconstruct the 3-dimensional distribution of electron density in the body without moving the patient or exciting source. The use of multiple energies permits selective imaging of different body tissues as noted for standard projection radiography.

A currently preferred embodiment has the following parameters:

For the storage ring, the electron energy is on the order of 142 Mev (See Table I for $CO_2$ laser). The average beam current is 300 mA. The interaction cross-section $\eta = 1$ mm$^2$. The storage ring parameter is 6 meters, and the electron repetition time $T_o = 20$ nsec. The interaction region is 1.5 meters, and the interaction time of the interaction region $T_i = 5$ nsec. The length of each bunch is 30 cm, and the electron bunch has a pulse length time $T_e = 1$ nsec. The frequency of encounters f in the interaction region is 50 MHz. The number of electrons in each bunch $N_e = 1.9 \times 10^9$.

For the laser, a $CO_2$ laser is used and has a photon energy $h\nu_1 = 0.124$ eV. The photon pulse length is 10 nsec. The repetition time period is 10 $\mu$sec with a frequency of 100 KHz. The pulse energy is 20 joules. The pulse power is 10 MW, and the average power is 10 KW. The number of photons in each pulse is $5 \times 10^{18}$. The attenuation at the mirrors in the optical cavity is about 2% per pass, and the number of passes per pulse is 50.

For the interaction region, the luminosity is $5 \times 10^{41}$ m$^{-2}$ sec$^{-1}$. The scattering cross-section $\sigma$ for 0.5% energy beam resolution is $2.4 \times 10^{-30}$ m$^2$. The collimating half angle $\theta_c = 0.5$ mrad. The number of photons per sec at 40 Kev is $1.2 \times 10^{12}$ photons/sec. The produced X-ray pulse duration is 1 $\mu$sec, and is repeated every 10 $\mu$sec. The number of photons per each produced X-ray pulse is $1.2 \times 10^6$ photons. The polarization is $1 - 2.5 \times 10^{-5} \approx 100\%$.

A typical two-dimensional scanning on an area 500 mm$^2 \times$ 500 mm$^2$ requires about $10^{10}$ photons to allow a 0.5% energy resolution count in the conical beam. In the above numerical example, this is accomplished by using $10^4$ X-ray pulses. The complete scan will be completed in about 100 msec. This is in contrast to 15 sec-20 sec scans with current mechanical scan projection radiography systems.

It will be understood that each of the elements described above, or two or more together, may also find a useful application in other types of constructions differing from the types described above.

While the invention has been illustrated and described as embodied in a method of and arrangement for producing X-rays, it is not to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. A method of irradiating an object with X-rays in a desired range suitable for medical diagnostic and therapeutic, or industrial testing, purposes, comprising the steps of:
   (a) passing a multitude of incoming electrons at a predetermined energy level in one direction along a predetermined path through an interaction region;
   (b) directing a multitude of incoming photons at a predetermined energy level along a direction opposite to the one direction through the interaction region and into colliding relationship with the incoming electrons, whereby outgoing photons are propagated at an increased energy level by the Compton scattering effect substantially along the one direction towards the object to be X-rayed;
   (c) controlling the energy level of the incoming electrons to convert the outgoing photons to X-rays within the desired range;
   (d) guiding the X-rays towards the object to be irradiated; and
   (e) said directing step including the step of generating the incoming photons from a light source, and directing them in said one direction, and reflecting the incoming photons for propagation back along the same path in said opposite direction while the electrons are passed in the one direction, said reflecting taking place between the object and the interaction region, such that said X-rays may be directed at a surface of the object confronting the interaction region without restriction from the object.

2. The method as defined in claim 1, wherein said passing step includes the step of magnetically acting on the electrons to cause the same to repeatedly circulate in a closed loop.

3. The method as defined in claim 1, wherein said controlling step includes the step of energizing the incoming electrons to energy levels such that the outgoing photons will lie in the desired range from about 0.5 Kev to about 250 Kev.

4. The method as defined in claim 1, wherein said controlling step includes the step of energizing the incoming electrons to energy levels such that the outgoing photons will lie in the desired range from about 20 Kev to about 100 Kev for medical diagnostic purposes.

5. The method as defined in claim 1, wherein said controlling step includes the step of energizing the incoming electrons to energy levels such that the outgoing photons will lie in the desired range from about 30 Kev to 250 Kev for therapy purposes.

6. The method as defined in claim 1, wherein said controlling step includes the step of energizing the incoming electrons to energy levels such that the outgoing photons will lie in the desired range from about 0.5 Kev to 100 Kev for elemental analysis purposes.

7. The method as defined in claim 1, wherein the said passing, directing and controlling steps are performed to generate X-rays having a polarized characteristic.

8. The method as defined in claim 1, wherein the said passing, directing and controlling steps are performed to generate X-rays having a conical beam configuration with a narrow angle of divergence.

9. The method as defined in claim 1, wherein said generating step includes generating said incoming photons from a collimated light source.

10. The method as defined in claim 1, wherein the said passing, directing and controlling steps are performed to generate X-rays having a narrow frequency band characteristic.

11. The method as defined in claim 1; and further comprising the step of varying the direction of propagation of the X-rays produced by the Compton effect to scan the object.

12. The method as defined in claim 11, wherein said varying step includes the step of changing the spatial position of the interaction region.

13. The method as defined in claim 12, wherein said changing step includes the step of magnetically deflecting the electrons passing through the interaction region to an offset position.

14. The method as defined in claim 13, wherein said changing step also includes the step of moving the incoming photons in space so as to maintain the coincidence of the same with the offset position of the electrons.

15. The method as defined in claim 14; and further comprising the step of tuning the frequency of the X-rays to any desired value within the desired range.

16. An apparatus for irradiating an object with X-rays in a desired range suitable for medical diagnostic and therapeutic, or industrial testing, purposes, comprising:
  (a) means for passing a multitude of incoming electrons at a predetermined energy level in one direction along a predetermined path through an interaction region;
  (b) means for directing a multitude of incoming photons at a predetermined energy level along a direction substantially opposite to the one direction through the interaction region and into colliding relationship with the incoming electrons, whereby outgoing photons are propagated at an increased energy level by the Compton scattering effect substantially along the one direction towards the object to be X-rayed;
  (c) means for controlling the energy level of the incoming electrons to convert the outgoing photons to X-rays within the desired range;
  (d) means for guiding the X-rays towards the object to be irradiated; and
  (e) said directing means including means for generating the incoming photons from a light source and directing them in said one direction, and means for reflecting the incoming photons for propagation back along the same path in said opposite direction while the electrons are passed in the one direction, said reflecting taking place between the object and the interaction region, such that said X-rays may be directed at a surface of the object confronting the interaction region without restriction from the object.

17. The apparatus as defined in claim 16, wherein said passing means includes a housing bounding an internal chamber, means for evacuating said internal chamber, and means for causing electrons to circulate in a closed loop having said path as a portion thereof in said internal chamber, including magnet means arranged along said loop.

18. The apparatus as defined in claim 17, wherein said magnet means is so distributed along said loop that said path is substantially straight.

19. The apparatus as defined in claim 18, wherein said magnet means includes two magnet devices each extending along a substantially semi-circular course and so oriented relative to the other magnet device at a predetermined distance therefrom that the electrons travel between said magnet devices in said straight path in said one direction and in another straight path parallel to said other direction.

20. The apparatus as defined in claim 17, wherein said passing means further includes means for accelerating electrons and injecting the same into said loop.

21. The apparatus as defined in claim 16, wherein said directing means includes means for repeatedly reflecting the incoming photons for propagation in both of said directions in said path for interaction of the incoming photons with the incoming electrons during the propagation of said incoming photons in said opposite direction.

22. The apparatus as defined in claim 21, wherein said light source comprises a laser; and wherein said reflecting means includes two mirrors arranged at opposite sides of said laser so as to define an optical cavity and include said interaction region between themselves.

23. The apparatus as defined in claim 22, wherein said laser is disposed outside of said interaction region.

24. The apparatus as defined in claim 16; and further comprising means for scanning the object to be X-rayed by electromagnetically varying the direction of propagation of the X-rays.

25. The apparatus as defined in claim 24, wherein said scanning means includes means for magnetically deflecting the electrons so as to change the spatial position of said path.

26. The apparatus as defined in claim 25, wherein said magnetically deflecting means includes at least two deflecting magnets arranged across said interaction region from one another, and operative for shifting the spatial position of said path with respect to the initial position thereof by magnetically acting on the incoming electrons traveling along the same.

27. The apparatus as defined in claim 26, wherein said scanning means further includes means for moving the incoming photons in space so as to maintain the coincidence thereof with the electrons in the shifted path.

28. The apparatus as defined in claim 27, wherein said moving means includes an optical scanner.

29. The apparatus as defined in claim 16; and further comprising means for tuning the frequency of the X-rays to a selected value within the desired range.

30. The apparatus as defined in claim 16, wherein said generating means comprises a collimated light source.

31. A method of irradiating an object with X-rays in a desired range suitable for medical diagnostic and therapeutic, or industrial testing, purposes, comprising the steps of:
(a) passing a multitude of incoming electrons at a predetermined energy level in one direction along a predetermined path through an interaction region;
(b) directing a multitude of incoming photons at a predetermined energy level along a direction opposite to the one direction through the interaction region and into colliding relationship with the incoming electrons, whereby outgoing photons are propagated at an increased energy level by the Compton scattering effect substantially along the one direction towards the object to be X-rayed;
(c) controlling the energy level of the incoming electrons to convert the outgoing photons to X-rays within the desired range;
(d) guiding the X-rays towards the object to be irradiated; and
(e) opto-magnetically scanning the object with the X-rays produced by the Compton effect, including magnetically deflecting the electrons in the interaction region to an offset position, and optically maintaining the direction of the photons in space such that the photons continue to travel along a direction opposite to the one direction through the interaction region and into colliding relationship with the incoming electrons.

32. The method as defined in claim 31, wherein the X-rays are a highly directional conical beam with a narrow angle of divergence.

33. The method as defined in claim 31, wherein the X-rays have a narrow band frequency characteristic, and wherein said controlling step includes the step of tuning the narrow band X-rays to a desired value, and wherein said guiding step is performed by guiding the tuned, narrow band X-rays to the object.

34. The method as defined in claim 31, wherein the X-rays are polarized, and wherein said guiding step is performed by guiding the polarized X-rays to the object.

35. The method as defined in claim 31, wherein said step of opto-magnetically scanning includes varying the incident angle of impingement on the object of the X-rays produced by the Compton effect.

36. Apparatus for irradiating an object with X-rays in a desired range suitable for medical diagnostic and therapeutic, or industrial testing, purposes, comprising:
(a) means for passing a multitude of incoming electrons at a predetermined energy level in one direction along a predetermined path through an interaction region;
(b) means for directing a multitude of incoming photons at a predetermined energy level along a direction opposite to the one direction through the interaction region and into colliding relationship with the incoming electrons, whereby outgoing photons are propagated at an increased energy level by the Compton scattering effect substantially along the one direction towards the object to be X-rayed;
(c) means for controlling the energy level of the incoming electrons to convert the outgoing photons to X-rays within the desired range;
(d) means for guiding the X-rays towards the object to be irradiated; and
(e) means for opto-magnetically scanning the object with the X-rays produced by the Compton effect including means for magnetically deflecting the electrons in the interaction region to an offset position and means for optically maintaining the direction of the photons in space such that the photons continue to travel along a direction opposite to the one direction through the interaction region and into colliding relationship with the incoming electrons.

37. The apparatus as defined in claim 36; and further comprising means for independently diverting a portion of the incoming electrons along another path remote from said predetermined path, and means for guiding the diverted electrons towards the object for radiation therapy purposes.

38. The apparatus as defined in claim 36, wherein said interaction region has a predetermined length, and wherein said means for directing is operative for generating pulses of photons, each pulse having a length in space from a pulse front to a pulse end substantially equal to twice said predetermined length of the interaction region.

39. The apparatus as defined in claim 38, wherein said directing means includes a pair of reflecting mirrors bounding an optical cavity, and wherein the photon pulses repeatedly reflect between the mirrors, and wherein the electrons successively interact with the photon pulses.

40. The apparatus as defined in claim 36; and further comprising detector means for detecting the flux of the X-rays impinging thereon, and for generating a counting signal indicative of the detected flux; means for electronically scanning the object with the X-ray beam, and for generating a steering signal indicative of the position of the scanning beam; and means for processing the counting and steering signals to determine the location of a scattering reaction in the object.

41. The apparatus as defined in claim 40, wherein said detector means includes a substantially planar two-dimensional radiograph detector located downstream of the object as considered in the direction of the guiding of the X-rays towards the object, said detector being operative for detecting the flux of the X-rays transmitted from the object for two-dimensional radiography purposes.

42. The apparatus as defined in claim 40, wherein said detector means includes a radiographic detector located at more than one side of the object, said detector being operative for detecting the flux of the X-rays transmitted from the object for the three-dimensional radiography purposes.

43. In trace elemental analysis, a method of irradiating a test sample with X-rays in a desired range suitable for industrial testing purposes, comprising the steps of:
(a) passing a multitude of incoming electrons at a predetermined energy level in one direction along a predetermined path through an interaction region;
(b) directing a multitude of incoming photons at a predetermined energy level along a direction opposite to the one direction through the interaction region and into colliding relationship with the incoming electrons, whereby outgoing photons are propagated at an increased energy level by the Compton scattering effect substantially along the one direction towards the test sample;

(c) controlling the energy level of the incoming electrons to convert the outgoing photons to X-rays within the desired range;

(d) guiding the X-rays towards the test sample to be irradiated; and (e) opto-magnetically scanning the object with the X-rays produced by the Compton effect, including magnetically deflecting the electrons in the interaction region to an offset position, and optically maintaining the direction of the photons in space such that the photons continue to travel along a direction opposite to the one direction through the interaction region and into colliding relationship with the incoming electrons.

* * * * *